US00PP29923P3

(12) United States Plant Patent
Hansen

(10) Patent No.: US PP29,923 P3
(45) Date of Patent: Nov. 27, 2018

(54) ***HEUCHERA* PLANT NAMED 'WILD ROSE'**

(50) Latin Name: ***Heuchera* hybrid**
Varietal Denomination: Wild Rose

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/530,028

(22) Filed: Nov. 21, 2016

(65) Prior Publication Data

US 2018/0146605 P1 May 24, 2018

(51) Int. Cl.
*A01H 5/12* (2018.01)
*A01H 5/02* (2018.01)

(52) U.S. Cl.
USPC ..... Plt./440
CPC ..... *A01H 5/02* (2013.01); *A01H 5/12* (2013.01)

(58) Field of Classification Search
USPC ..... Plt./440
CPC . A01H 5/02; A01H 5/025; A01H 5/00; A01H 5/12; A01H 6/80
See application file for complete search history.

(56) References Cited

U.S. PATENT DOCUMENTS

PP19,585 P2 * 12/2008 Delabroye ..... A01H 5/02 Plt./440
PP26,788 P2 * 5/2016 Hurd ..... A01H 5/12 Plt./440
PP26,894 P2 * 6/2016 Hansen ..... A01H 5/02 Plt./440

* cited by examiner

*Primary Examiner* — June Hwu

(57) ABSTRACT

The new and distinct hybrid of *Heuchera* plant named 'Wild Rose' with large foliage with rounded apices and lobe, leaf blades of rosy-purple with dark mahogany surrounding the veins and without silver overlay between the veins. Panicles are dark burgundy with matching buds that open for a rosy-pink effect for five weeks beginning late spring. The new plant is vigorous and produces large clumps with many large leaves.

1 Drawing Sheet

Botanical denomination: *Heuchera* hybrid.
Variety denomination: 'Wild Rose'.

BACKGROUND OF THE INVENTION

The present invention relates to a new and distinct cultivar of Coral Bells in the Saxifragaceae family and given the cultivar name of 'Wild Rose'. *Heuchera* 'Wild Rose' was hybridized by the inventor on Apr. 3, 2013 at a wholesale perennial nursery in Zeeland, Mich., USA and initially assigned the breeder code 13-811-1. The seed or female parent was a proprietary unreleased hybrid known only by the breeder code 12-45-01 (not patented) consisting of 'Pistache' U.S. Plant Pat. No. 19,585, 'Caramel' U.S. Plant Pat. No. 16,560, and *Heuchera hallii*, and the pollen or male parent was 'Georgia Plum' U.S. Plant Pat. No. 24,507.

*Heuchera* 'Wild Rose' was first selected in the fall of 2013 and passed final evaluation in the fall of 2014 from among thousands of other seedlings from the same cross and hundreds of other crosses. *Heuchera* 'Wild Rose' has been asexually propagated by division at the same nursery in Zeeland, Mich. in 2014 and by sterile shoot-tip tissue culture propagation, and the resultant plants have remained stable and continued to exhibit the same characteristics as the original plant for multiple generations.

No plants of *Heuchera* 'Wild Rose' have been sold, in this country or anywhere in the world, prior to the filing of this application, nor has any disclosure of the new plant been made prior to the filing of this application with the exception of that which was disclosed within one year of the filing of this application, and was either derived directly or indirectly from the inventor.

BRIEF SUMMARY OF THE INVENTION

The female parent, 12-45-01 is no longer available for detailed comparison. In comparison to 'Georgia Plum', *Heuchera* 'Wild Rose' has foliage with darker veins, less silver overlay and more purple between the veins and rounder apices and lobes. Compared to 'Pistache', the new plant has foliage with purple and dark mahogany veins and pink flowers and 'Pistache' lacks dark mahogany veins and has green foliage in the spring and yellow foliage in mid-summer. Compared to *Heuchera hallii*, the new plant is larger in habit, with foliage of purple and dark mahogany veins, and the flowers are pink and on longer panicles. Other similar coral bells include: 'Grape Expectations' U.S. Plant Pat. No. 26,894 which has foliage with more silver overlay between the veins and flowers of pink compared with the near white flowers of 'Grape Expectations'. Compared to 'Blackberry Ice' U.S. Plant Pat. No. 26,788, the new plant has no silver overlay between the veins, and the flowers are pink and not cream.

*Heuchera* 'Wild Rose' differs from its parents as well as all other coral bells known to the applicant in the following combined traits:

1. The large foliage has rounded apices and lobes.
2. Leaf blades are rosy-purple with dark mahogany surrounding the veins.

3. Leaves stay rosy-purple without getting silver overlay between the veins.
4. Panicles of dark burgundy produce matching buds that open to rosy-pink floral effect for five weeks beginning late spring.
5. The new plant is vigorous and produces large clumps and many large individual leaves.

BRIEF DESCRIPTION OF THE DRAWINGS

The photographs of the new plant demonstrate the overall appearance of the plant including the unique traits. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
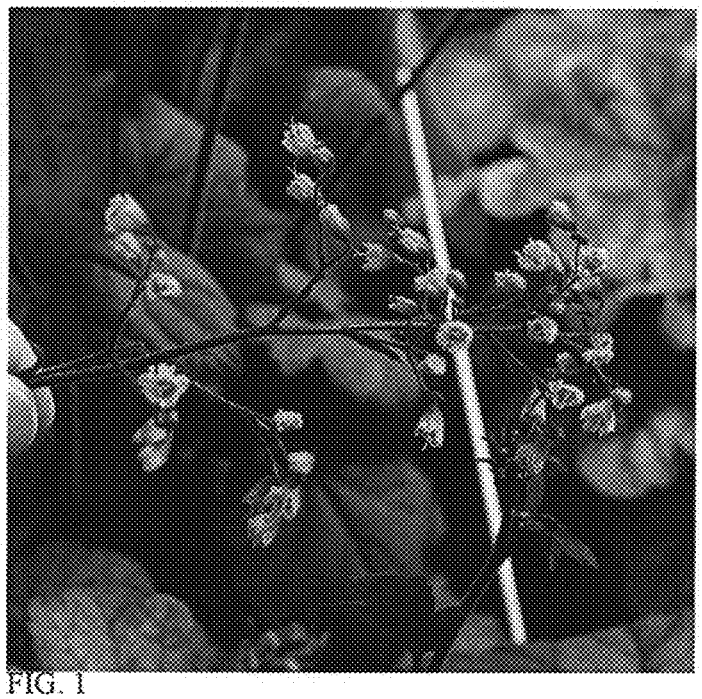
FIG. 1 shows a close-up of the flowers.
Figure 2:
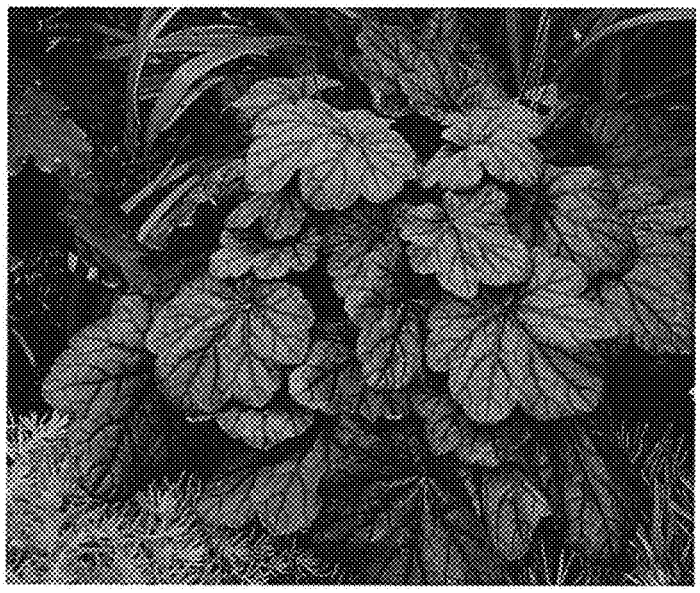
FIG. 2 shows a one-year-old plant in a container just before flowering.

The following description is based on a one-year-old plant growing in a partially shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2001 edition of The Royal Horticultural Society Colour Chart except where common dictionary terms are used.

Parentage: Female or seed parent was the proprietary unreleased hybrid known only by the breeder code 12-45-01 (not patented) and the pollen or male parent was 'Georgia Plum';

Plant habit: Hardy herbaceous perennial with basal rosette of foliage; mounded foliage about 25 cm tall and 48 cm in diameter with scapes to about 65 cm long; stems to about 4.0 cm long and 2.0 cm diameter at base with about 15 to 18 leaves per stem and five main stems per plant;

Roots: Fibrous, finely branched;

Growth rate: Rapid, rooting from cutting in two weeks and finishing in three-liter container in about 3 months;

Foliage: Cordate, minutely puberulent adaxial and abaxial; palmately shallowly lobed with five main lobes dissected less than one-fifth the way to petiole; apex and lobe apices rounded, base cordate to auriculate with basal lobes typically overlapping about 0.5 cm; margins crenate to mucronate, hirsutulous; lustrous adaxial and abaxial; held nearly horizontal; margin weakly undulated;

Leaf blade size: To about 13.5 cm wide and 12.5 cm long, average about 12.0 cm wide and 11.0 cm long;

Leaf color: Spring and young emerging leaves adaxial between RHS 187B and RHS 187C and with no silver and dark green marbling surrounding the veins, spring young emerging leaves abaxial nearest RHS N186D; mature mid-season leaves adaxial nearest RHS N77B between the veins and between RHS N186B and RHS 187A surrounding the veins, abaxial mature mid-season leaves nearest RHS N186C; fall and winter color adaxial variable, nearest RHS N77B, N199A and RHS 199A with area surrounding veins nearest RHS N186A, fall and winter color abaxial blend between RHS N79A and RHS N79B;

Leaf quantity: Dense, about 80 per plant;

Veins: Palmate, hirsutulous abaxial and adaxial; costate abaxial, slightly impressed adaxial;

Vein color: Emerging or early spring adaxial between RHS 187B and RHS 187C with emerging spring abaxial between RHS N79C and RHS N79B; mid-season and flowering time adaxial between RHS N77A and RHS N77B, mid-season and flowering time abaxial nearest RHS N79B;

Petiole: Terete, base amplexicaul; with pubescent hairs to about 2.0 mm long; average about 11.0 cm long and about 3.0 mm diameter above stipule and 12.0 mm at base including stipule;

Petiole color: Emerging leaf blend between RHS N79C and RHS N79B; mature leaf near base of petiole nearest RHS N186C, distally between RHS 146A and RHS 146B with blush of nearest RHS N186C;

Stipule: At base of petiole, about 1.6 cm long and about 1.3 cm wide at base;

Stipule color: Adaxial between RHS N79A and RHS N79B, abaxial nearest RHS N79B;

Peduncle: Panicle; terete; stiff; pubescent; upright; to about 65.0 cm long and 3.5 mm diameter at base, average about 62 cm tall and 3.0 mm diameter; about fourteen per plant with up to 175 flowers per panicle, average about 150; tightly-branched panicle with up to 21 branches up to 8.0 cm long and 1.0 mm diameter decreasing distally, average 16 branches per panicle; lower branches mostly upright becoming drooping distally; flower density moderate;

Flowering longevity: Panicle effective for about four to five weeks;

Peduncle color: Blend between RHS 187A and RHS N186B;

Pedicel: Terete, pubescent; about 4.0 mm long and 0.3 mm diameter, attitude drooping;

Pedicel color: Between RHS N186D and RHS 187C;

Buds one day prior to opening: Ellipsoid; rounded apex and attenuate base; puberulent to glandular; about 4.5 mm long and 2.5 mm diameter;

Bud color one day prior to opening: Basal portion nearest RHS 61A, distally becoming between RHS 64A and RHS 64B;

Flower: Perfect, campanulate, actinomorphic, about 8.0 mm long and 6.0 mm in diameter at face; individual flowers lasting about 4 days on plant or as cut flower;

Flower attitude: Drooping;

Calyx: Five, apex rounded, base fused in proximal 4.5 mm to form hypanthium; pubescent abaxial, glabrous adaxial; about 8.0 mm long and 6.0 mm wide;

Calyx color: Aabaxial basal half nearest RHS 70B, distally lightening to nearest RHS 73D;

Petals: Five, oblanceolate to spatulate, rounded apex and attenuate base, entire, glabrous abaxial, puberulent adaxial, about 5.5 mm long and 1.0 mm wide in middle;

Petal color: Abaxial and adaxial distally nearest RHS N155C, adaxial and abaxial base lighter than RHS 155D;

Androecium: Five adnate to adaxial sepal about 1.0 mm above base;

*Filaments.*—Five, thin, glabrous; about 3.0 mm long and less than 0.3 mm diameter; color white, lighter than RHS 155D.

*Anthers.*—Ellipsoidal, distinct, basifixed, longitudinal; color nearest RHS 25B.

*Pollen.*—Abundant; color nearest RHS N25A.

Gynoecium: One, two-beaked; half-inferior; bifid style with pistil split at ovary; 8.5 mm long;

*Style.*—Bifid; split apart at apex of ovary; about 6.0 mm long and about 0.5 mm diameter; color lighter than RHS N155D distally and proximally nearest RHS 62D.

*Stigma.*—Acute apex, about 0.1 mm diameter, color lighter than RHS 155D.

*Ovary.*—Half-inferior, about 2.5 mm long and 2.0 mm diameter; ellipsoidal to globose, base rounded; color nearest RHS 150D.

Fruit and seeds have not yet been observed;

Disease and pest tolerance: The new plant grows best with ample moisture and drainage in either part sun or full shade. Cold hardy from USDA zones 4 to 9. Other resistance and tolerance outside of that normal for *Heuchera* is not known.

It is claimed:

1. The new and distinct coral bells plant named *Heuchera* 'Wild Rose' as herein described and illustrated.

* * * * *